United States Patent [19]

Jeffrey et al.

[11] Patent Number: 5,277,877
[45] Date of Patent: Jan. 11, 1994

[54] ROOM AIR PURIFIER

[75] Inventors: Robert E. Jeffrey, Chino, Calif.; R. Malone Hodges, Oracle, Ariz.; William F. Dempster, Oracle, Ariz.; Robert G. Hahn, Oracle, Ariz.

[73] Assignee: Space Biospheres Ventures, Oracle, Ariz.

[21] Appl. No.: 740,850

[22] Filed: Aug. 6, 1991

[51] Int. Cl.$^5$ ............................................... A61L 9/00
[52] U.S. Cl. ...................................... 422/124; 47/79; 47/81; 422/120
[58] Field of Search .................. 422/4, 120, 124, 299, 422/300; 47/66, 58, 1.4, 18, 39, 79, 81, 62

[56] References Cited

U.S. PATENT DOCUMENTS

| | | | |
|---|---|---|---|
| 180,242 | 7/1876 | Niest | 47/79 |
| 2,198,150 | 4/1940 | Barnhart | 47/62 |
| 2,837,868 | 6/1958 | Skerritt | 47/79 |
| 3,298,133 | 1/1967 | Courtright | 47/61 |
| 3,550,319 | 12/1970 | Gaines, Jr. | 47/39 |
| 4,732,591 | 3/1988 | Tujisawa et al. | 55/279 |
| 4,975,251 | 12/1990 | Saceman | 422/124 |
| 4,996,792 | 3/1991 | Holtkamp, Sr. | 47/81 |

OTHER PUBLICATIONS

Houseplants Indoor Air Pollutants and Allergic Reactions, B. C. Wolverton, NASA Technology Labs., MS 395229, Dec. 1986.

Primary Examiner—Robert J. Warden
Assistant Examiner—Amalia Santiago
Attorney, Agent, or Firm—Christie, Parker & Hale

[57] ABSTRACT

An indoor air purifier has a base and a container on the base with a layer of soil supported above a lower water bath occupying the bottom of the container. The container is fitted on top of the base such that the container can freely rotate upon the base. Room air is drawn into the base and is passed from the base into the bottom of the container through a duct connected between the two. Air passing from the base is directed downwardly into the water bath before passing upwardly into the soil layer. The air passes through the soil layer and is discharged from the soil's surface back into the room. Contaminant gases and particulates are removed from the air through contact with the soil layer and are metabolized by microorganisms contained within the soil, producing carbon dioxide and water. The water bath humidifies the air being passed through it and maintains a stable degree of moisture in the lower portion of the soil layer. Water lost through evaporation is replenished through a sleeve passing downward from the soil's surface to the water bath. A water bottle inverted within the sleeve maintains a substantially constant water level. Plants may be grown in the soil layer to aid in purification and to provide an attractive room decor.

30 Claims, 2 Drawing Sheets

ROOM AIR PURIFIER

FIELD OF THE INVENTION

This invention relates to an indoor air purifier using a soil bed reactor and a water bath through which room air is passed for removal of particulates and oxidation of noxious gases by aerobic microorganisms in the soil.

BACKGROUND OF THE INVENTION

The environment within homes, offices, and other indoor facilities is often contaminated with a variety of noxious and toxic gases. Such gasses include carbon monoxide, methane, sulfur dioxide, hydrogen sulfide, $NO_x$, and a broad variety of organic vapors as well. Although these gases may be attributed to outdoor sources, many are prevalent within the indoor environment due to either the captive location of an indoor facility near an outdoor source or to gas emitting activities occurring within the indoor facility itself.

Indoor activities that are known to generate noxious or toxic materials include tobacco smoking, cooking, open fireplaces, faulty appliances, or a variety of other normal activities. These noxious or toxic materials are characterized differently in terms of their effects or impact on the environment. Some may merely have an unpleasant odor; others may accumulate and soil surfaces; while others may be dangerous, actually posing a health hazard to those exposed to the materials. Studies have shown, for example, that exposure to second-hand tobacco smoke significantly increases ones risk of developing lung cancer. Additionally, it has been found that a high proportion of homes contain latent carbon monoxide concentrations responsible for vague disorders such as lassitude and headaches at concentrations far below levels known to produce overt symptoms of toxicity.

Particulate matter is also commonly found in the indoor environment. Tobacco smoking, for example, generates both particles and gasses. Organic aerosols, dust particles, pollen, and minute organisms are further examples of particles typically found floating in the air. Such particles may pose a health hazard due to either the chemical nature of the particle or by the particle's physical size. Environmental standards have been promulgated for particles smaller than about ten micrometers because particles of this size are known to penetrate much deeper into the lungs than coarser particles.

Therefore, because such toxic and noxious materials constitute known health risks and because these materials are prevalent indoors where a majority of time is spent, it is clearly desirable to reduce the concentrations of such noxious and toxic materials in the indoor environment.

Many devices have been marketed over the years in an attempt to assist in this regard. Negative ion generators are regarded by some as effective. However, their effectiveness is largely dependent on particle size, therefore, they are not well suited for the removal of a broad spectrum of gases. Room air fresheners only serve to mask the odors but do nothing to remove the gases or particulate matter from the air. Activated charcoal filters may also be used, however, they are fairly expensive and their effectiveness is dependent on the condition of the charcoal's activated sites. This type of filter losses its effectiveness progressively with use and there is no means to determine the point when the filter becomes ineffective. The result is that either the filter is prematurely discarded or is kept in service long after its useful life.

It is, therefore desirable to provide an air purifier for indoor use for reducing the concentrations of particulates and noxious and toxic gases in the air. It is desirable that this apparatus operate for long periods without being exhausted or require costly replacements. It is desirable that it be effective with respect to a broad spectrum of noxious and toxic materials. It is desirable that it be simple to operate and require low-cost materials. It is also highly desirable that it be attractive since it becomes a permanent fixture in the indoor environment.

SUMMARY OF THE INVENTION

There is, therefore, provided in practice of this invention according to a preferred embodiment, an indoor air purifier in the form of a base and an open container on top of the base. The container comprises an upper chamber, having a layer of soil supporting the growth of aerobic microorganisms, and a lower chamber having a water bath. Means are provided for fitting the container on top of the base such that the container can freely rotate upon the base. Means are provided for drawing air from a room into the base, passing the air upwardly into the container through a duct connecting the base to the bottom portion of the container, directing the air passed from the base downwardly into the water bath, dispersing the rising air bubbles formed by passing air through the water bath for minimizing noise, passing the air from the water bath upwardly through a soil bed retainer plate and into the soil layer, and discharging the air from the surface of the soil back into the room.

In such an air purifier the particulates in the air that are not removed by passing through either a prefilter or water bath are caught in the soil layer and removed. Many types of noxious and toxic gases are absorbed by the soil layer through contact with soil moisture. The aerobic microorganisms in the soil metabolize a broad spectrum of vapors and remove them from the air. In such an air purifier the water bath both humidifies the air being passed through it and maintains a constant degree of moisture in the lower portion of the soil layer. Means are also provided for maintaining a constant level of water in the water bath.

Such an air purifier is also aesthetically pleasing since the soil layer is suitable for supporting growth of plants selected by the homeowner or office worker.

BRIEF DESCRIPTION OF THE DRAWINGS

These and other features and advantages of the present invention will be appreciated as the same becomes better understood by reference to the following detailed description when considered in connection with the accompanying drawings wherein.

DETAILED DESCRIPTION

Figure 1:
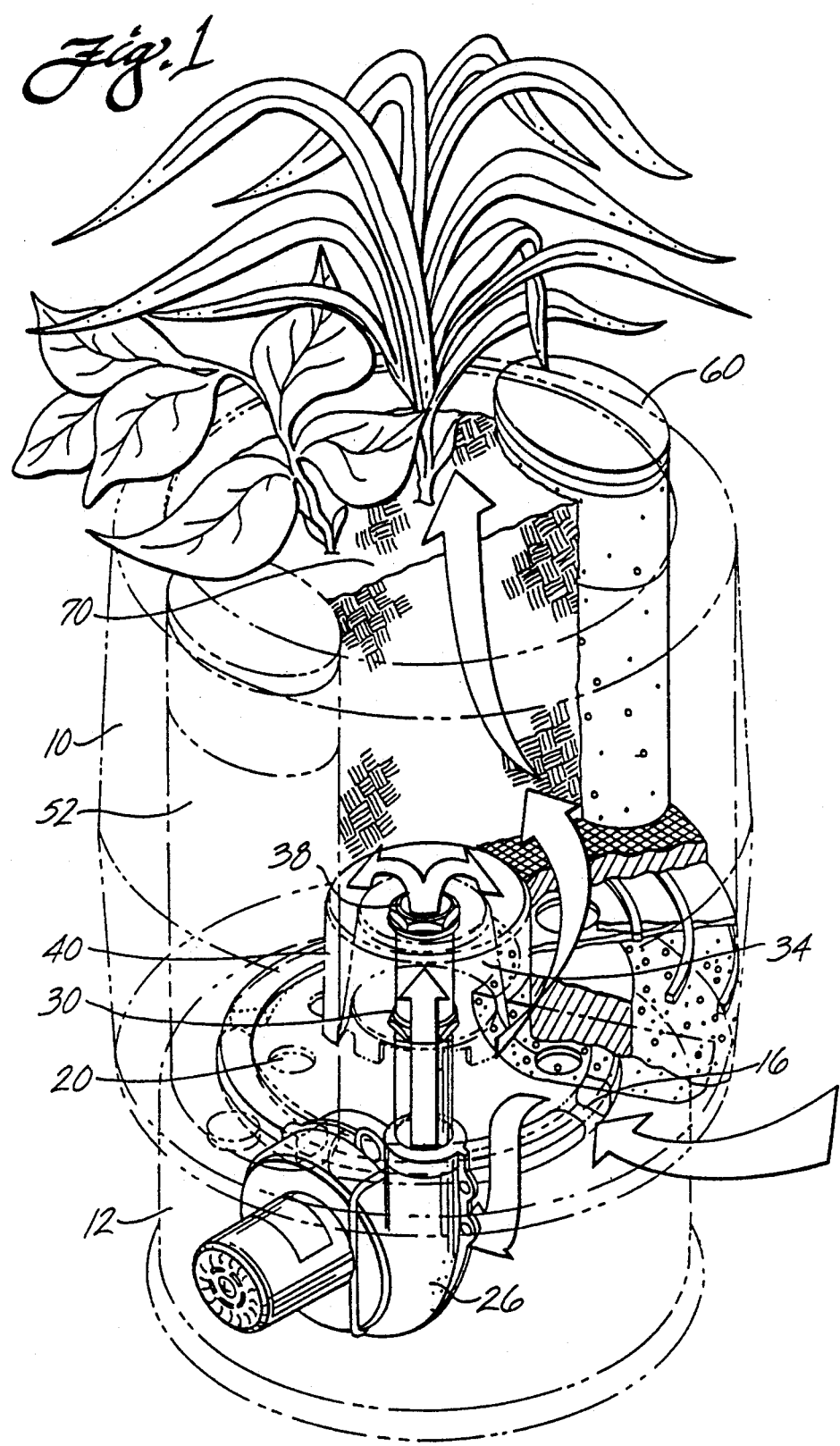
FIG. 1 illustrates a preferred embodiment of soil bed reactor indoor air purifier in semischematic cutaway perspective view.
Figure 2:
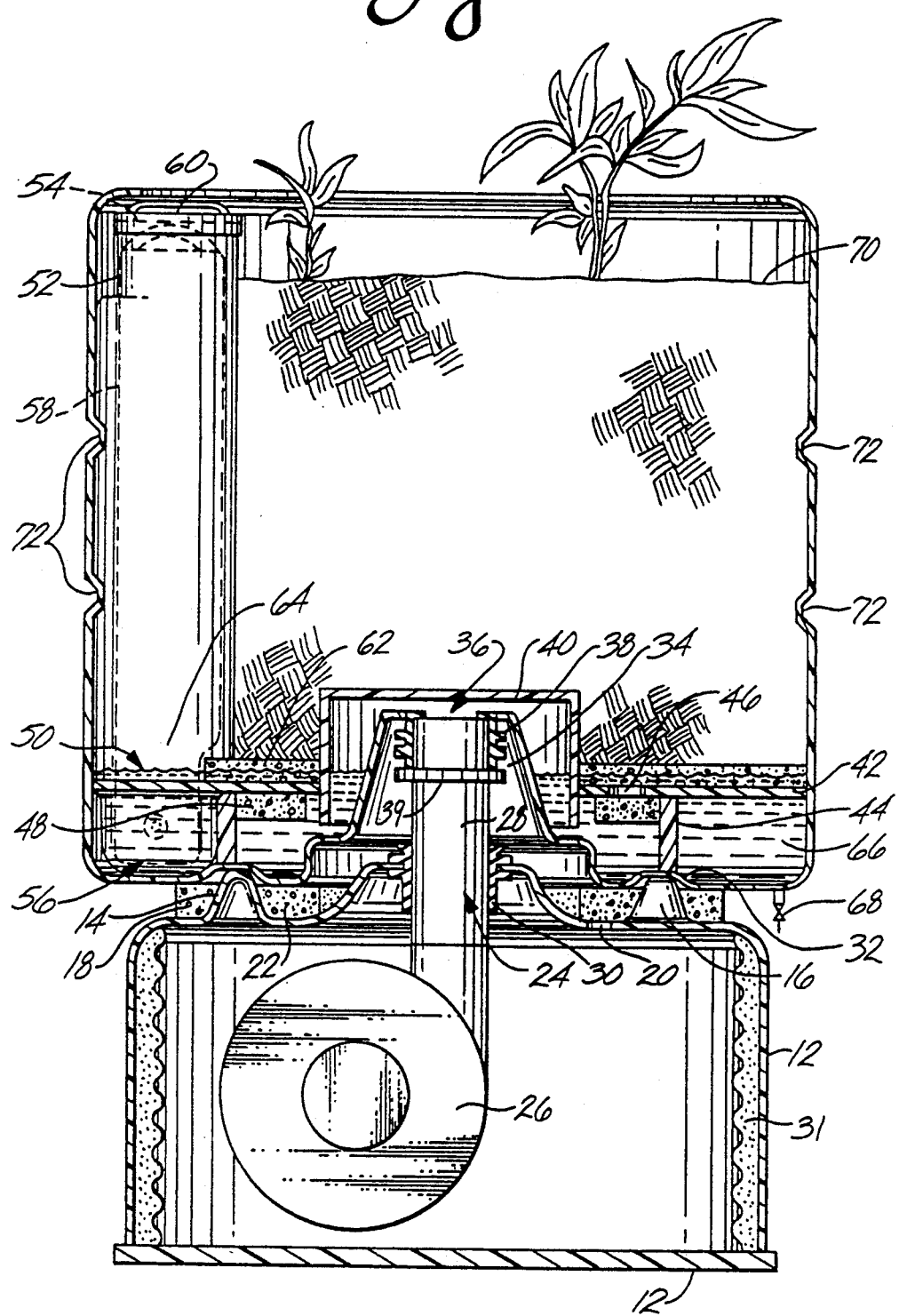
FIG. 2 illustrates the soil bed reactor indoor air purifier in semi-schematic vertical cross section.

In an exemplary embodiment, an indoor air purifier has an open top, largely impermeable container 10 sitting on a base 12. The container and base each may, for example, be a fiberglass or polypropylene cylinder, box, or the like which may be colored or decorated in a manner suitable for permanent display in a home, office, or the like. Preferably, the horizontal cross section of the base is in the range of from 0.2 to one square meter. An exemplary embodiment is in the form of a cylindrical base having closed top surface and a hollow inner cavity. The diameter of base is 50 centimeters and it stands 30 centimeters high.

A raised rail 14 extends upwardly two centimeters from the principal top surface of the base in a circular pattern concentric within the diameter of the base. The rail is divided into a plurality of segments, each of which has a circumferential length of ten centimeters and a radial width of two or three centimeters. The rail segments are spaced apart circumferentially to form a plurality of air intake openings 16 as the gaps between the rails. The air intake gaps 16 have a length of five centimeters.

A removable primary lint filter 18 extends around the outer circumference of the base's raised rail and shields the air intake openings. The primary lint filter comprises an open cell, permeable foam element having a radial thickness of four centimeters and a sufficient height to fill the gap between the base and the container sitting on the base.

A plurality of air inlet openings 20 extend from the base's outer surface to its hollow inner cavity. The air inlet openings have a diameter of three centimeters and are positioned in a circular pattern concentric within the diameter of the rails. A secondary lint filter 22 sits on top of the base and shields the base's air inlet openings. The secondary lint filter comprises an open cell, permeable foam element having a thickness of three centimeters. The lint filters also serve to minimize fan noise.

A single air duct opening 24 exists in the center of the base and extends between the base's outer surface and its hollow inner cavity.

A conventional impeller type centrifugal air blower 26 is mounted within the hollow cavity of the base such that its intake opening is exposed to the base's air inlet openings. The blower's outlet opening is connected to a duct 28 that extends upwardly from the base's cavity through the base's duct opening and away from the base. The duct has an inside diameter of five centimeters and is sealed within the duct opening through the use of an appropriately sized rubber grommet 30. The blower is sufficient for delivering about 450 cubic meters of air per day at a static pressure head of about eight centimeters. An impeller type blower is preferred since it is relatively quiet. The base is lined with "egg crate" foam 31 for noise reduction. A typical unit has a noise level of only about 50 db.

The container 12 is fitted to the base through the interaction of the base's rail with a grooved recess 32 molded into the underside of the container. The container's grooved recess is positioned concentrically within the diameter of the container and is sized to accommodate the base rail. The container's underside is generally a closed surface except for a central opening.

The complementary rail on the base and groove in the bottom of the container prevent the container from sliding sideways off of the base and also permit rotation of the container on top of the base. A plant may be planted in the container and it is often desirable to rotate the plant to change its exposure to light. Thus, it is desirable to employ a round container so it has the same aspect regardless of how rotated. A circular base under the container is aesthetically pleasing. In addition, the generally cylindrical shapes are economically formed by rotary molding of recycled polypropylene or the like.

At the center of the container's underside the bottom surface of the container flares upwardly into the body of the container forming a volcano-shaped recess 34 which projects upwardly inside the container. The recess extends inwardly into the container fifteen meters at the center of the container. At the center of the container the volcano has an duct opening 36.

The container is fitted onto the base such that the duct 28 extending upwardly from the base surface is inserted through the container's duct opening with the duct's opening flush with the top lip of the volcano. The duct is sealed within the container's opening by an appropriately sized rubber grommet 38. The rubber grommet is secured around the circumference of the duct by a hose clamp 39.

Inside the bottom of the container a circular air chamber cap 40 surrounds the raised portion of the volcano and the duct. The air chamber cap is cylindrical in shape having one closed end and one open end. The cap is positioned over the top of the volcano such that its closed end sits near the duct opening and the open end is suspended above the volcano's base near the bottom of the container. The air chamber cap has a diameter of twenty centimeters and its height is fifteen centimeters.

A circular soil bed retainer plate 42 is attached to the outer wall of the air chamber cap. The retainer plate extends horizontally away from the outside circumference of the air chamber cap to the inside wall of the container. The retainer plate has its inside diameter connected to the outside of the air chamber cap and has an outer diameter similar to the inside diameter of the container. Attached to the underside of the retainer plate is a circular support ring 44 that extends downwardly from the retainer plate and rests against the bottom of the container. The support ring has a diameter five centimeters greater than the inside diameter of the retainer plate and a height of seven or eight centimeters, which defines the distance between the retainer plate and the bottom of the container.

The air chamber cap, retainer plate and support ring are connected together. This supports the bottom of the cap above the bottom of the container so that air forced through the duct by the blower in the base flows downwardly and then laterally beneath the bottom of the cap.

The retainer plate has a plurality of air transfer openings 46 through the plate in a circular pattern concentric around the air chamber cap.

An aeration pad 48 is mounted to the underside of the retainer plate and positioned such that it covers the air transfer openings. The aeration pad is a circular, open cell, permeable polypropylene foam element that occupies the underside area of the retainer plate between the air chamber cap wall and the retainer support ring. The aeration pad has a thickness of two centimeters. The aeration pad acts as a diffuser to break up large air bubbles passing through water in the bottom of the container.

The retainer plate has one or more water bottle sleeve openings 50 along its outer marginal edge sized to accommodate the passage of one or more water bottle sleeves 52. Two sleeves are used in a exemplary embodiment. Each water bottle sleeve extends vertically along the inside wall of the container from the container's rim to near its bottom. The inlet opening of the sleeve 54 is located near the container's open rim and the dispensing end 56 extends down through the retainer plate opening and rests against the container's bottom.

An inverted water bottle 58 is removably received within each water bottle sleeve. Each water bottle has a volume of three liters. Typical water usage is less than two liters per day. A removable cap 60 is slidably mounted over the inlet opening of the sleeve to hide the end of the bottle. The sleeve has a somewhat flattened cylindrical shape with a width of fifteen centimeters and a height similar to that of the container. A hydrophilic permeable separator pad 62 is placed on top of the retainer plate. The separator pad is a circular element covering the top surface of the retainer plate with a thickness of about two centimeters. The separator pad has an inside diameter equal to the outside diameter of the air chamber cap and has an outside diameter equal to the container's diameter The separator pad also has one or more water bottle sleeve openings 64 along its outer marginal edge sized to accommodate the passage of one or more water bottle sleeves.

A water bath 66 occupies the lower chamber of the container formed between the soil bed retainer plate and the bottom of the container. The water bath contains a water volume in the range of from 15 to 20 liters. The water level in the bottom of the container is maintained below the level of the top of the central volcano. Thus, the grommet sealing the duct through the bottom of the container needs to only prevent appreciable air leakage and need not be water tight. A drain plug 68 is located near the bottom of the container's lower chamber to facilitate the draining of the water, if desired.

A soil layer 70 occupies the upper chamber of the container above the separator pad to the container's open rim. The typical depth of soil layer is a little less than a half meter. The exposed top surface of the soil layer is typically a few centimeters below the open rim of the container.

As used herein, "soil" means a porous hydrophilic medium which supports growth of aerobic microorganism populations which oxidize airborne organic contaminants. It may comprise soil indigenous to the user's area which may be augmented with organic additives, peat moss, sand and clay mixtures, small ceramic or plastic particles or rings, commercially available potting soil, or the like.

Potting soil is preferred since it is hydrophilic, rich in organic nutrients, stable, permeable, readily available and inexpensive. A typical potting soil includes sand, a small amount of clay, other mineral grains, and organic particles or fibers, and may include adjuvants such as bits of plastic foam for enhancing permeability, and conventional chemical fertilizers. The soil used may also include small additions of alkaline materials for neutralizing acid gasses such as $SO_2$ and $NO_x$. A suitable "soil" comprises 40% perlite or pumice, 10% composted steer manure or mushroom soil, 30% peat moss, 20% local top soil.

Preferably the layer of soil has a thickness and permeability which permits air to be drawn through the soil with an apparent residence time of approximately 10 seconds. A preferred thickness of the soil layer is about forty-five centimeters. Such a thickness insures a sufficient residence time of air passing through the soil for adsorption on soil particles so that the microorganisms may oxidize a substantial proportion of noxious gases in the air. A flow through the soil of 400 to 500 cubic meters per day is desirable.

It is desirable that plants be grown in the soil bed reactor. The plants may be selected for their attractive appearance in the home or office. Recommended plants include lacy tree philodendron (Philodendron selloum), Chinese evergreen (Aglonema modestum), golden pothos (Soindapsus elatum), peace lily (Spathiphyllum clevlandii), corn plant (Uranceana fragrans massangeana) or warneckei (Dracaena deremensis "Warneckei"). The plants help to maintain the porosity of the soil and plant debris maintains soil nutrients which help support the growth of microorganisms. A preferred type of plant chosen should be a hardy foliage variety that has some value in cleaning the air.

When the room air purifier is operating, air is drawn from the room into the base 12 through the primary lint filter 18, the air intake openings 16 in the rail, the secondary lint filter 22, the air inlet openings 20 through the top of the base, and into the intake of the air blower 26 located inside the base's hollow cavity. Inside the base, the air blower's outlet is attached to the duct 28 that extends upwardly through the duct opening of the base 24 and into the duct opening of the container's underside 36. The air blower passes the room air from the base into the container through the duct connecting the two.

Upon entering the container the air passed through the duct from the base is deflected by the air chamber cap 40 downwardly into the water bath 64. The air is then bubbled through the water bath and the rising air bubbles are dispersed or diffused through contact with the aeration pad 48. The aeration pad breaks up large bubbles which may form in the water bath into myriad small bubbles. This significantly reduces noise from the air purifier. Without the diffuser in the water bath a bubbling or gurgling sound is produced. After leaving the aeration pad the air travels upwardly through the air transfer openings in the soil bed retainer plate and passes into the separator pad. The air then passes upwardly through the separator pad and enters the base of the soil layer. The air travels upwardly through the volume of the soil layer and is discharged from the soil's surface back into the room.

As the air passes through the layer of soil, aerosols, particles, organic vapors and other gases which may be undesirable are adsorbed in the soil and employed by aerobic organisms in the soil as a source of nutrients. Excellent removal of toxic and noxious gases and vapor is obtained by using such a soil bed reactor.

Some of the undesirable material in the air is dissolved or suspended in the water bath, too. Furthermore, as water evaporates from the water bath, salts and scale tend to accumulate. It is therefore desirable to intermittently drain the water via the drain plug and treat the water bath area with a little vinegar or the like.

A wall wiper 72 extends inwardly away from the inside wall of the container towards the center of the container. The wiper is positioned a reasonable distance below the surface of the soil layer and extends into the soil bed. The wall wiper interrupts any channeling of air that may occur between the soil bed and the container wall through redirecting the flow through the principal portion of the soil layer. The wall wiper extends away from the container wall a couple centimeters.

It is desirable that the plants cultivated in the soil layer of the air purifier have equal access to the sun to ensure maximum plant growth. Accordingly, the interaction between the base's rail 14 and the container's grooved recess 32 permits the container to be rotated freely about the base. Through the periodic rotation of the container the plants contained in the soil can be afforded equal access to a window or other fixed light source.

The air purifier's water bath serves two important interrelated functions; the water bath both humidifies the air being passed through it and it maintains a constant degree of moisture in the lower portion of the soil bed. Maintaining a reasonable amount of moisture throughout the soil bed is important for the effective absorption of gases, filtering of particulates, and the sustained growth of the plants and microorganisms.

The lower portion of soil is kept moist through effective liquid contact with the water bath and through the passing of humidified air through the soil. The level of the water bath extends about midway into the thickness of the separator pad, which is about 2 cm thick. The water migrates upwardly through the thickness of the hydrophilic separator pad and into the lower portion of the soil bed through wicking. However, in order to maintain the desired moisture content throughout the entire soil bed, it is desirable that the top surface of the soil be lightly watered on a regular basis, typically every week to ten days. Fertilizer may be included with such top watering.

The volume of the water bath is not static due to both evaporation into the atmosphere and absorption for plant growth. Accordingly, water must be added to the water bath to ensure the efficient absorption of gases and toxins. Water is added to the water bath by filling the water bottle 58 and inverting it into the water bottle sleeve 52. The water bottle sleeve facilitates the replenishing of the water bath by providing a direct channel connecting the surface of the soil layer to the water bath.

The water level in the bath is maintained by the inverted bottles. The bottles are shaped complementary to the inside of the water bottle sleeves, fitting within the sleeves and resting against the water bottle sleeves' contoured shoulder formed to allow the water bottle sleeve to pass through the soil bed retainer plate 42. When the water level drops, air can enter the bottle and additional water flows into the bath to restore its level. Refilling the water bottles every week or so is sufficient for maintaining a desired water level in the bath, depending on relative humidity and the hours per day that the blower is kept running.

Although but one exemplary embodiment of soil bed reactor room air purifier has been described and illustrated herein, many variations will be apparent to those skilled in the art. For example, other complementary connections between the base and the container on top of the base may be used. The rail may be on the bottom of the container and the groove on the base, for example. The retainer plate for the soil, diffuser for bubbles in the water and hydrophilic separator pad may be made integrally of a somewhat thick rigid permeable material. Since many such modifications may be made, it is to be understood that within the scope of the following claims, this invention may be practiced otherwise than specifically described.

What is claimed is:

1. A soil bed reactor room air purifier comprising:
   a base;
   a container having an upper chamber retaining a layer of soil containing aerobic microorganisms, and a lower chamber retaining a water bath;
   means for fitting the container on top of the base;
   means for drawing air from a room into the base; and
   means for passing the air from the base into the container and through the water bath, then through the layer of soil and discharging the air into the room.

2. An air purifier as recited in claim 1 wherein the means for fitting the container on the base comprises complementary surface features on the top of the base and an underside of the container for inhibiting the container from sliding off of the base and permitting rotation of the container on the base.

3. An air purifier as recited in claim 2 wherein the complementary surface features comprise a circular rail on the base and a circular groove in the bottom of the container, the rail being divided into a plurality of circumferentially extending segments with gaps between the segments for permitting radial air flow between the base and the container.

4. An air purifier as recited in claim 1 wherein the means for drawing air from a room into the base comprises:
   a plurality of air intake openings through said base extending from outside the base to a hollow cavity inside the base; and
   a blower inside the cavity for drawing air from a room through the intake openings and into the cavity and for discharging air upwardly into the container.

5. An air purifier as recited in claim 4 wherein the air intake openings are through the top of the base beneath the container and further comprising means for spacing the container away from the base a sufficient distance to permit air flow therebetween.

6. An air purifier as recited in claim 1 wherein the means for passing air comprises:
   an opening in the top of the base;
   an opening in an underside of the container at an elevation above the bottom of the container;
   a duct connecting the opening in the base to the opening in the container;
   the water bath in the bottom of the container being at an elevation below the opening in the underside of the container;
   means for directing air from the duct through the water bath; and
   a soil retainer plate for supporting the layer of soil and having a plurality of openings permitting transfer of air from the water bath to the soil layer.

7. An air purifier as recited in claim 6 comprising means for maintaining the water bath at a level for wetting a lower portion of the soil layer.

8. An air purifier as recited in claim 7 wherein the means for maintaining water level comprises a bottle inverted in the water bath with an opening at a desired water level.

9. An air purifier as recited in claim 1 wherein the water bath is in the bottom of the container and further comprising:
   a hollow bottle sleeve mounted within the container extending from an upper opening at the surface of the soil to a lower opening adjacent to the water bath; and an inverted water bottle removably fitted within the hollow bottle sleeve for replenishing water lost through evaporation.

10. An indoor air purifier for removing oxidizable gases and particulates from room air comprising:
a container having an upper chamber retaining a layer of soil capable of supporting growth of aerobic microorganisms and a lower chamber retaining a water bath below the layer of soil;
means for supporting the layer of soil above the water bath;
means adjacent to the means for supporting the layer of soil for passing room air serially through the water bath and upwardly through the layer of soil; and
porous means immersed in the water bath for diffusing air bubbles formed by passing air through the water bath.

11. An air purifier as recited in claim 10 wherein the means for supporting the layer of soil comprises a horizontal retainer plate having a plurality of air transfer openings through the plate.

12. An air purifier as recited in claim 11 wherein the porous means comprises a porous diffuser element attached to the retainer plate's underside covering the plurality of air transfer openings, the diffuser element operating to diffuse air bubbles formed from forcing air through the water bath.

13. An air purifier as recited in claim 12 further comprising a hydrophilic pad fitted on top of the retainer plate for separating the water bath from the soil and for wetting a lower portion of the layer of soil.

14. An indoor air purifier for removing oxidizable gases and particulates from room air comprising:
a container, a layer of soil in the container capable of supporting growth of aerobic microorganisms;
a water bath in the container below the layer of soil;
means in fluid communication with said container for passing room air serially through the water bath and upwardly through the layer of soil comprising:
an air duct,
an air chamber cap means for directing the room air flow from the duct downwardly below the surface of the water bath; and
a horizontal soil retainer plate for supporting the layer of soil and having a plurality of air transfer openings permitting the passage of the room air from the water bath upwardly into the soil layer; and
means for diffusing air bubbles formed by passing the room air through the water bath.

15. An air purifier as recited in claim 14 comprising means for maintaining the level of the water bath so that the soil retainer plate is immersed in the water bath and a lower portion of the layer of soil is in effective liquid contact with the water bath.

16. An indoor air purifier comprising:
a base;
a container having a permeable soil layer and a water bath below the soil layer;
means for supporting the soil layer above the water bath;
means for fitting the container on top of the base;
means for drawing air from a room into the base and then passing the air through the water bath and upwardly through the soil layer; and
means for continually maintaining the water bath at a substantially constant level.

17. An air purifier as recited in claim 16 wherein the means for maintaining water level comprises an inverted bottle having an opening immersed in the water.

18. An air purifier as recited in claim 16 wherein the base comprises:
a hollow member with a top surface of a shape complementary to the bottom of the container; and
a plurality of air intake openings permitting room air to enter a hollow cavity inside the base.

19. An air purifier as recited in claim 16 wherein the means for fitting the container on top of the base comprises:
a raised rail integral with and extending upwardly from a top surface of the base; and
a groove complementary to the rail recessed into an underside surface of the container.

20. An air purifier as recited in claim 19 wherein the rail is divided into a plurality of segments defining a plurality of openings for air to pass to air intake openings on top of the base.

21. An air purifier as recited in claim 16 wherein the container comprises:
a hollow cylindrical member having a closed bottom portion and an open top portion;
a horizontal soil retainer plate inside the hollow cylindrical member;
an upper soil storage chamber;
a lower water bath reservoir;
the horizontal soil retainer plate being located between the upper chamber and lower reservoir; and
a hydrophilic pad fitted on top of the soil retainer plate for separating the water bath from the soil and for wetting a lower portion of the layer of soil.

22. An air purifier as recited in claim 16 wherein the means for drawing air from the room into the base and passing it through the container's water bath and soil layer comprises:
means for drawing air from the room into the base;
a duct communicating between the top of the base and underside of the container;
an air chamber cap means for directing air from the duct downwardly into the container's water bath; and
wherein the means for supporting the soil layer comprises a horizontal soil retainer plate below the soil for supporting the soil layer and having a plurality of air transfer openings permitting the passage of air from the water bath into the soil layer.

23. An air purifier as recited in claim 22 comprising a hydrophilic pad above the soil retainer plate and at least partially immersed in the water for separating the water bath from the soil and for wetting a lower portion of the layer of soil.

24. An air purifier as recited in claim 22 comprising means in the container for diffusing air bubbles formed by passing air through the water bath.

25. An air purifier as recited in claim 24 wherein the means for diffusing air bubbles comprises a permeable foam element below the retainer plate.

26. An air purifier as recited in claim 16 wherein the means for maintaining the water level in the water bath comprises:
a hollow bottle sleeve vertically mounted within the container extending downwardly from above the layer of soil to the water bath; and
an inverted bottle removably fitted within the bottle sleeve.

27. A soil bed reactor room air purifier comprising:

a hollow base;

a circular rail around a top of the base, the rail being divided into a plurality of circumferentially extending segments leaving gaps between the segments for passage of room air;

a plurality of openings in the top of the base inwardly from the rail for introducing room air into the base;

an open top container on top of the base;

a circular groove in the bottom of the container complementary to the rail on the base for permitting rotation of the container on the base;

a retainer plate in the container above the bottom of the container;

a layer of soil on top of the retainer plate containing microorganisms for metabolizing vapors carried in room air;

a bath of water in the bottom of the container;

a central duct between the base and the bottom of the container, the top of the duct being above the level of the water bath;

a blower in the hollow base connected to the duct for passing room air into the duct;

a cap surrounding the duct in the bottom of the container for deflecting air from the duct below the surface of the water bath; and openings through the retainer plate for passing air from the water bath into the lower portion of the layer of soil.

28. An air purifier as recited in claim 27 comprising a hydrophilic permeable support pad between the soil and the retainer plate, at least a portion of the support pad being immersed in the water bath.

29. An air purifier as recited in claim 28 comprising a permeable layer below the retainer plate for diffusing air bubbles formed by passing air through the water bath.

30. An air purifier as recited in claim 27 comprising:

a hollow bottle sleeve vertically mounted within the container extending downwardly from above the layer of soil to the water bath; and an inverted bottle removably fitted within the bottle sleeve for maintaining a substantially constant water level in the water bath.

* * * * *